United States Patent
Che et al.

(10) Patent No.: US 10,029,081 B2
(45) Date of Patent: Jul. 24, 2018

(54) MOLDING COMPACT, AND MANUFACTURING METHOD FOR TRANSDERMAL ABSORPTION SHEET

(71) Applicant: FUJIFILM Corporation, Tokyo (JP)

(72) Inventors: Yanlong Che, Ashigarakami-gun (JP); Takayoshi Oyamada, Ashigarakami-gun (JP); Junya Yoshida, Ashigarakami-gun (JP); Shotaro Ogawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 424 days.

(21) Appl. No.: 14/709,640

(22) Filed: May 12, 2015

(65) Prior Publication Data
US 2015/0238743 A1      Aug. 27, 2015

Related U.S. Application Data

(63) Continuation of application No. PCT/JP2013/080537, filed on Nov. 12, 2013.

(30) Foreign Application Priority Data

Nov. 13, 2012   (JP) ................................. 2012-249680

(51) Int. Cl.
   *B32B 3/30*      (2006.01)
   *A61M 37/00*     (2006.01)
   (Continued)

(52) U.S. Cl.
   CPC ....... *A61M 37/0015* (2013.01); *A61K 9/0021* (2013.01); *B29C 33/3857* (2013.01);
   (Continued)

(58) Field of Classification Search
   CPC ............. A61M 37/0015; A61K 9/0021; B29C 33/3857; B29C 33/40; B29C 33/424;
   (Continued)

(56) References Cited

U.S. PATENT DOCUMENTS

2011/0192562 A1   8/2011   Motoi et al.
2011/0195124 A1*  8/2011   Jin ....................... A61K 9/0021
                                                   424/486

FOREIGN PATENT DOCUMENTS

JP    2002-179824 A    6/2002
JP    2007-260351 A    10/2007
(Continued)

OTHER PUBLICATIONS

Machine Translation of JP-2012200572-A (Year: 2012).*
(Continued)

*Primary Examiner* — Daniel McNally
(74) *Attorney, Agent, or Firm* — Birch, Stewart, Kolasch & Birch, LLP (57) ABSTRACT

A molding compact for forming a transdermal absorption sheet on which a needle-shaped protruding part is arranged is a molding compact that is a laminate of: a first member having a needle-shaped recessed part formed on a front surface thereof, the needle-shaped recessed part being an inverse of the needle-shaped protruding part; a second member provided on a back surface of the first member, the second member being composed of a waterproof and moisture-permeable material; and a third member provided on a back surface of the second member, the third member being composed of a rigid body. Provided are a molding compact that makes it possible to prevent leakage of a drug-containing solution filled into the needle-shaped recessed part, and a manufacturing method for a transdermal absorption sheet using the molding compact.

9 Claims, 5 Drawing Sheets

(51) Int. Cl.
*A61K 9/00* (2006.01)
*B32B 37/10* (2006.01)
*B32B 37/00* (2006.01)
*B32B 25/20* (2006.01)
*B32B 27/26* (2006.01)
*B32B 27/28* (2006.01)
*B29C 33/38* (2006.01)
*B29C 33/40* (2006.01)
*B29C 33/42* (2006.01)
*B29L 31/00* (2006.01)

(52) U.S. Cl.
CPC ............ *B29C 33/40* (2013.01); *B29C 33/424* (2013.01); *B32B 3/30* (2013.01); *B32B 25/20* (2013.01); *B32B 27/26* (2013.01); *B32B 27/283* (2013.01); *B32B 37/025* (2013.01); *B32B 37/1018* (2013.01); *A61M 2037/0046* (2013.01); *A61M 2037/0053* (2013.01); *A61M 2207/10* (2013.01); *B29C 2033/385* (2013.01); *B29L 2031/756* (2013.01); *B29L 2031/7544* (2013.01); *B32B 2255/26* (2013.01); *B32B 2305/00* (2013.01); *B32B 2307/724* (2013.01); *B32B 2307/7265* (2013.01)

(58) Field of Classification Search
CPC ........... B32B 3/30; B32B 25/20; B32B 27/26; B32B 27/283; B32B 37/025; B32B 37/1018
See application file for complete search history.

(56) References Cited

FOREIGN PATENT DOCUMENTS

| JP | 2011-78617 A | 4/2011 | |
|----|--------------|--------|--|
| JP | 2012-200572 A | 10/2012 | |
| JP | 2012200572 A | * 10/2012 | ........ A61M 37/0015 |

OTHER PUBLICATIONS

Extended European Search Report dated May 10, 2017 in European Patent Application No. 17153451.4.
Extended European Search Report dated Jun. 9, 2016, issued in corresponding European Patent Application No. 13855117.1.
International Preliminary Report on Patentability, issued in PCT/JP2013/080537, dated Feb. 5, 2015.
International Search Report, issued in PCT/JP2013/080537, dated Feb. 25, 2014.
Written Opinion of the International Searching Authority, issued in PCT/JP2013/080537, dated Feb. 25, 2014.
English translation of the International Preliminary Report on Patentability (Forms PCT/IB/338 and PCT/IPEA/409), dated May 14, 2015, for International Application No. PCT/JP2013/080537.
Japanese Office Action for Japanese Application No. 2014-546986, dated Apr. 4, 2016, with a partial English translation.
A Chinese Office Action and Search Report, dated Sep. 1, 2016, for corresponding Chinese Application No. 201380059041.1, along with an English translation.

* cited by examiner

MOLDING COMPACT, AND MANUFACTURING METHOD FOR TRANSDERMAL ABSORPTION SHEET

CROSS-REFERENCE TO RELATED APPLICATIONS

This application is a Continuation of PCT International Application No. PCT/JP2013/080537 filed on Nov. 12, 2013, which claims priority under 35 U.S.C. § 119(a) to Japanese Patent Application No. 2012-249680 filed on Nov. 13, 2012. Each of the above application(s) is hereby expressly incorporated by reference, in its entirety, into the present application.

BACKGROUND OF THE INVENTION

Field of the Invention

The present invention relates to a molding compact for forming a transdermal absorption sheet on which a needle-shaped protruding parts are arranged, and a manufacturing method for the transdermal absorption sheet.

Description of the Related Art

Conventionally, most methods for administering a medicine (drug) through a living body surface, that is, a skin or a mucous membrane are mainly methods in which a liquid substance or a powdery substance is attached. However, the attachment region of these substances is limited to the surface of the skin. Therefore, the attached medicine and the like are sometimes removed by sweating or the contact of a foreign substance, and the administration of the proper dose is difficult. Further, when the medicine penetrates deep into the skin, it is difficult to surely control the penetration depth in the method utilizing such a penetration of the medicine by diffusion. Therefore, it is difficult to obtain a sufficient drug effect.

Therefore, there has been performed a method in which a transdermal absorption sheet having needle-shaped protruding parts arranged thereon is used, the needle-shaped protruding parts are inserted into the skin, and thereby the medicine is infused. As a method for forming such a transdermal absorption sheet, a cast molding method using a mold (cast) that includes needle-shaped recessed parts is known. A solution composed of a resin polymer and a drug is poured into the mold that includes the needle-shaped recessed parts. After drying, it is bonded to a fixing substrate, and the separation transfer is performed. It is thereby possible to obtain the transdermal absorption sheet.

The needles, each of which has a base diameter of 50 to 500 μm and a height of 50 to 200 μm, are arranged in an array. For performing the needling into the skin with no pain, it is preferable to use a thin needle that has a high aspect ratio and that has a pointed end as sharp as possible. Further, as this material, a material having biocompatibility and biodegradability is used. Moreover, a drug is previously added to the material, and the transdermal absorption sheet is bonded to the skin. It is thereby possible to release the drug into the skin.

However, in the cast molding method, since the needle-shaped recessed part of the mold has a very minute dimension, a problem occurs that the solution is not easily filled into the needle-shaped recessed part due to the air and surface tension. Hence, Japanese Patent Application Laid-Open No. 2011-78617 (hereinafter, "PTL 1") describes that a through hole penetrating to the opposite surface of the mold is provided at the bottom of the needle-shaped recessed part of the mold, whereby even when the air stays in the needle-shaped recessed part of the mold, the air easily comes out, so that the needle material can be filled into a recessed part of a stamper.

Further, in Japanese Patent Application Laid-Open No. 2012-200572 (hereinafter, "PTL 2"), the needle material filled into the needle-shaped recessed part of the mold is sucked from a through hole in a back surface of a base-member, at the timing when a step of applying a force such as drying stress and shearing force is performed, whereby the needle material is secured in the needle-shaped recessed part. Therefore, it is described that the separation of the needle material from the needle-shaped recessed part can be prevented against the force such as drying stress and shearing force.

SUMMARY OF THE INVENTION

However, in the manufacturing methods for the transdermal absorption sheet described in PTL 1 and PTL 2, there is a problem in that the drug-containing solution filled into the needle-shaped recessed part of the mold may leak from the through hole during the filling.

The present invention, which has been made in view of such circumstances, aims to provide a molding compact and a manufacturing method for a transdermal absorption sheet that make it possible to prevent the leakage of the drug-containing solution filled into the needle-shaped recessed part.

For achieving the above object, an aspect of the present invention provides a molding compact for forming a transdermal absorption sheet on which a needle-shaped protruding parts are arranged, the molding compact configured by laminating: a first member having needle-shaped recessed parts formed on a front surface thereof, the needle-shaped recessed parts being an inverse of the needle-shaped protruding parts; a second member provided on a back surface of the first member, the second member being composed of a waterproof and moisture-permeable material; and a third member provided on a back surface of the second member, the third member being composed of a rigid body.

By the compact configured by laminating the first member having the needle-shaped recessed part, which is the inverse of the needle-shaped protruding part, formed on the front surface, the second member provided on the back surface of the first member and composed of a waterproof and moisture-permeable material, and the third member provided on the back surface of the second member and composed of a rigid body, it is possible to prevent leakage of a drug-containing solution filled into the needle-shaped recessed parts.

It is preferable that the second member be low in liquid permeability compared to the first member and the third member, and the third member be high in rigidity compared to the first member and the third member. It is thereby possible to, more suitably, prevent the leakage of the drug-containing solution filled into the needle-shaped recessed part.

It is preferable that through holes each having a size of 1 μm or more and 50 μm or less be formed at pointed ends of the needle-shaped recessed parts of the first member. Since the through holes having a size of 1 μm or more and 50 μm or less are formed at the pointed ends of the needle-shaped recessed parts of the first member, even when air stays in the needle-shaped recessed parts of the first member, the air easily comes out. When the size of the through holes is 1 μm or more, the drug-containing solution is easily infused into the needle-shaped recessed parts so that the productivity is improved. Further, when the size of the through holes is 50 µm or less, the needling into the skin can be performed with no pain, because pointed ends of the needles of the manufactured transdermal absorption sheet have a size of 50 µm or less. Here, the size of the through holes, more preferably, should be 10 µm or more and 50 µm or less, and further preferably, should be 15 µm or more and 45 µm or less.

It is preferable that the waterproof and moisture-permeable material of the second member be a porous material having a pore size of 0.1 µm or more and 2.0 µm or less. When the pore size of the second member is 0.1 µm or more, the permeability of air is good, the filling of the solution is easy, and the productivity is good. Further, when the pore size of the second member is 2.0 µm or less, the deformation of the first member due to the suction can be prevented at the time of the manufacture of the transdermal absorption sheet to thereby prevent the leakage of the solution, even if the first member is composed of a soft material such as silicone rubber.

It is preferable that an air permeability of the second member and the third member be 3 seconds/100 cm$^3$ or more and 100 seconds/100 cm$^3$ or less.

When the air permeability of the second member and the third member is 3 seconds/100 cm$^3$ or more, the solution is easily filled into the needle-shaped recessed parts of the first member, resulting in a good productivity. When the air permeability of the second member and the third member is 100 seconds/100 cm$^3$ or less, the second member is hard to tear due to the suction at the time of the manufacture of the transdermal absorption sheet and the solution is unlikely to leak. Further, in the case where the air permeability is 100 seconds/100 cm$^3$ or less, the adhesiveness with the first member is good, which enables stable manufacture.

It is preferable that the first member and the second member be secured by adhesion or suction. The molding compact is configured by the adhesion-bonding or pressure-bonding the second member composed of a waterproof and moisture-permeable material which allows permeation of air but not of liquid, to the first member. In such the molding compact, a gap does not appear on a contact surface between the first member and the second member. Therefore, it is possible to prevent the leakage of the drug-containing solution filled into the needle-shaped recessed parts from the contact surface between the first member and the second member.

For achieving the above object, an another aspect of the present invention provides a manufacturing method for a transdermal absorption sheet including: a step of filling a solution obtained by mixing a drug and a polysaccharide, into the needle-shaped recessed parts of the above-described molding compact; a step of making a solidified matter by drying and solidifying the solution filled into the molding compact; and a step of separating the solidified matter from the molding compact.

In the manufacturing method for the transdermal absorption sheet according to the another aspect of the present invention, it is preferable that vacuum suction be performed from a back surface of the third member of the molding compact, in the step of filling the solution. By performing the vacuum suction from the third member composed of a rigid body, even when air stays in the needle-shaped recessed parts, it is possible to stably remove the air.

In the transdermal absorption sheet manufactured by the manufacturing method for the transdermal absorption sheet according to the another aspect of the present invention, the drug-containing solution filled into the needle-shaped recessed parts does not leak in the manufacturing process, and therefore, it is possible to provide a transdermal absorption sheet with no defect.

The present invention can provide a molding compact and a manufacturing method for a transdermal absorption sheet that make it possible to prevent the leakage of the drug-containing solution filled into the needle-shaped recessed parts.

DETAILED DESCRIPTION OF THE EMBODIMENTS

Hereinafter, a molding compact and a transdermal absorption sheet according to an embodiment of the present invention, and the manufacturing methods are described.

Figure 1A:
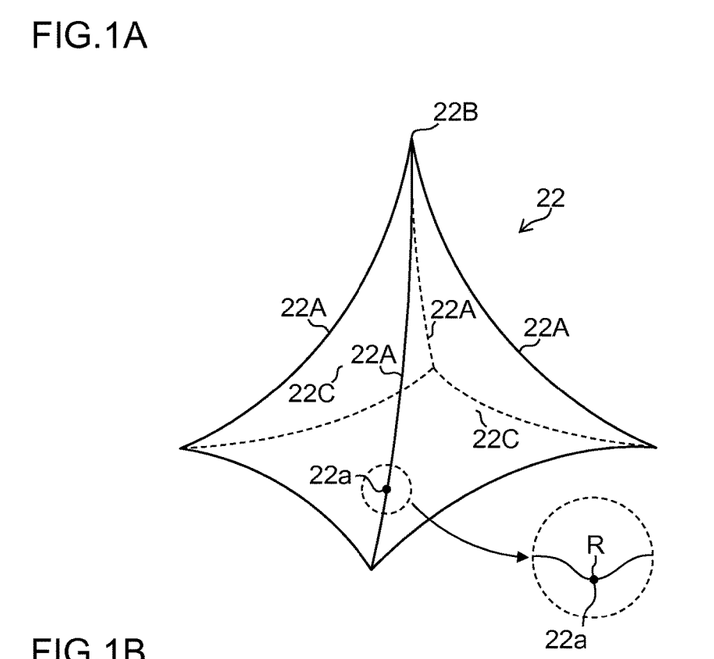
FIG. 1A is a perspective view of a pyramidal micro-needle of a transdermal absorption sheet.
Figure 1B:
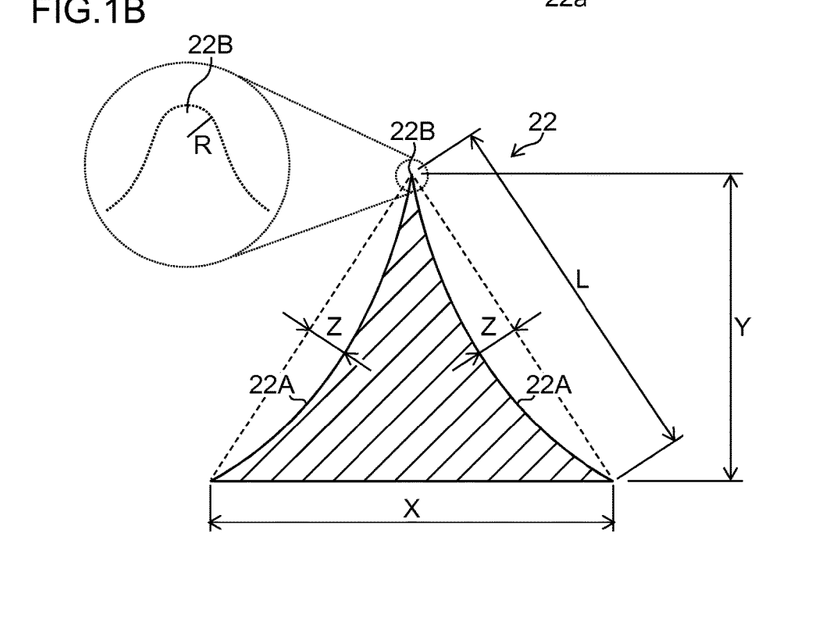
FIG. 1B is a cross-section view of the pyramidal micro-needle of the transdermal absorption sheet.

FIGS. 1A and 1B show a perspective view and cross-section view of a pyramidal micro-needles of a transdermal absorption sheet that is manufactured by a manufacturing method according to the present invention.

As shown in FIGS. 1A and 1B, as for the shape of a micro-needle (minute protruding part) 22 to be formed on a transdermal absorption sheet, it is necessary (1) that the pointed end is sufficiently sharp and the diameter of the needle to be inserted into the skin is also sufficiently thin (the aspect ratio of length/diameter is high), and (2) that the strength is sufficient (the needle is not bent), for pricking the skin surface to a depth of hundreds µm with the micro-needle 22.

Therefore, for meeting the requirement of (1), a thin and sharp shape is necessary, but this conflicts with (2). In the case of being too thin, it is bent at the pointed end or the base. In the case of being too thick, the pricking cannot be performed. Therefore, as shown in FIG. 1A, it is preferable that a ridge line 22A of the micro-needle 22 have a shape in which it curves to the inside of the micro-needle. Such a shape can make the pointed end sufficiently sharp, and furthermore can make it hard to bend because of a wide base. Further, it is preferable that the ridge lines 22A, 22A of the pyramidal micro-needle overhang relative to a pyramidal surface 22C between the ridge lines.

As for the shape of the micro-needle 22, it is preferable that a single side X of the base surface be in a range of 0.1 µm or more and 1000 µm or less, and the height be 0.3 µm or more and 3000 µm or less. More preferably, the single side X should be in a range of 10 µm or more and 400 µm or less, and the height should be 30 µm or more and 1200 µm or less.

Then, when the length of the line segment connecting the start point and end point of the ridge line is L, it is preferable that the maximum depth Z of the curve of the ridge line 22A be 0.04×L or more and 0.2×L or less. Further, the curvature radius R of a micro-needle pointed end 22B, which indicates the sharpness of the micro-needle, preferably, should be 20 µm or less, and more preferably, should be 10 µm or less.

Figure 2A:
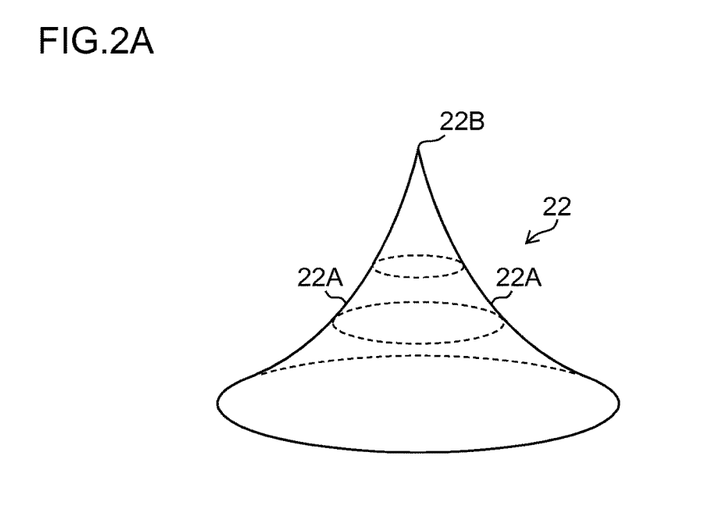
FIG. 2A is a perspective view of a conical micro-needle of a transdermal absorption sheet.
Figure 2B:
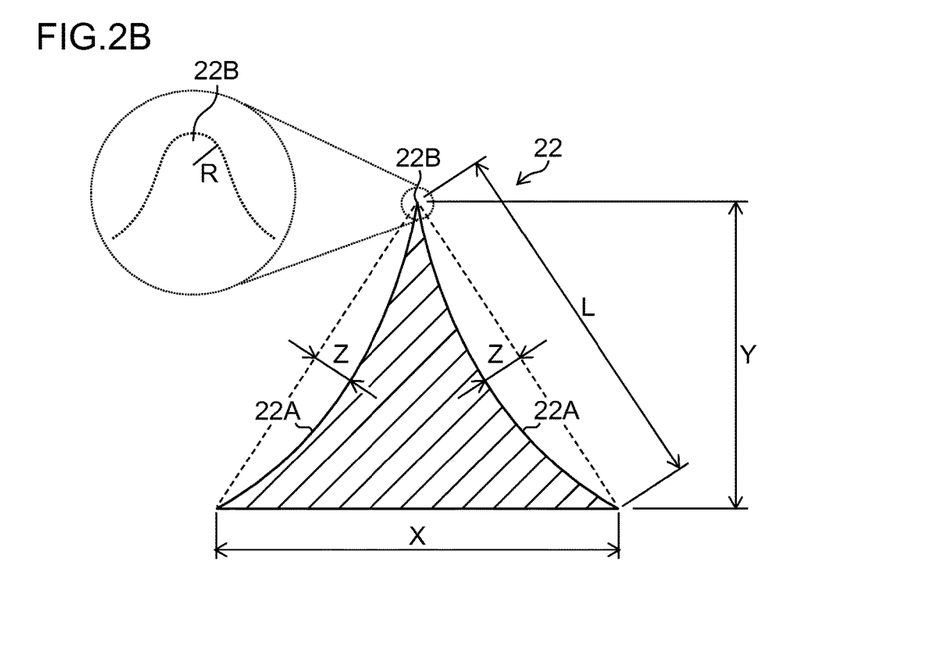
FIG. 2B is a cross-section view of the conical micro-needle of the transdermal absorption sheet.

Here, although FIGS. 1A and 1B show the square-pyramidal micro-needle 22, a conical micro-needle shown in FIGS. 2A and 2B and another pyramidal micro-needle, preferably, should have the same size. Here, in the case of a conical shape, the diameter X of the base surface, preferably, should be in a range of 0.1 µm or more and 1000 µm or less, and more preferably, should be in a range of 50 µm or more and 300 µm or less. Further, when the length of the line segment connecting the start point and end point of the slant height of the conical surface is L, it is preferable that the maximum depth Z of the curve of the conical surface be 0.04×L or more and 0.2×L or less.

As described above, the micro-needle array is an array of minute protruding parts, and for facilitating the pricking of the skin surface, it is preferable that the pointed end of the protruding part 22 be sufficiently sharp, and the curvature radius R of the pointed end of the protruding part 22 be 50 µm or less.

Figure 3:
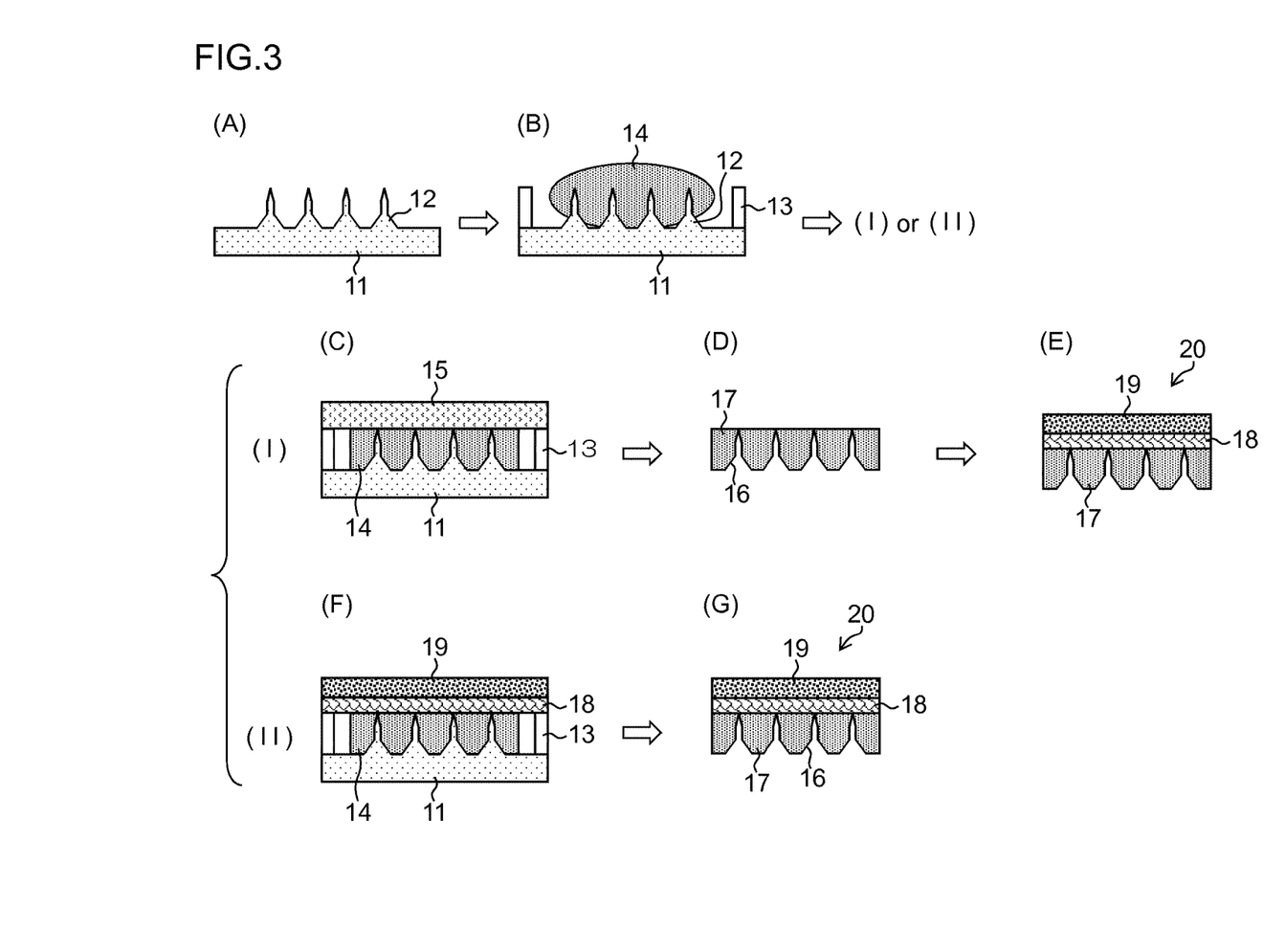
FIG. 3 is a process drawing showing an example of a manufacturing method for a molding compact according to the present invention.

Next, a manufacturing method for a molding compact is described. FIG. 3 shows a process drawing of a manufacturing method for a molding compact.

First, the production of an original form is performed. Specifically, in an original form producing step, an original form 11 (exemplified in portion (A) of FIG. 3) for producing a molding compact by which the transdermal absorption sheet is manufactured is produced.

The producing method for the original form 11 comes in two types. In the first method, after photoresist is applied on a Si substrate, the exposure and the development are performed, and then, the etching is performed by the RIE (reactive ion etching) or the like. Thereby, an array of conical shape parts (protruding parts) 12 is produced on the front surface of the original form 11. Here, when performing the etching such as the RIE, it is possible to form the conical shape, by performing the etching from an oblique direction while rotating the Si substrate.

In the second method, a substrate of a metal such as Ni is processed using a cutting tool such as a diamond bit, and thereby, an array of shape parts 12 such as the square pyramid is formed on the front surface of the original form 11.

Next, the production of the molding compact is performed.

A molding compact 20 according to the embodiment of the present invention is configured by laminating a first member 17 having needle-shaped recessed parts, each of which is the inverse of the needle-shaped protruding part, formed on the front surface, a second member 18 provided on the back surface of the first member 17 and composed of a waterproof and moisture-permeable material, and a third member 19 provided on the back surface of the second member 18 and composed of a rigid body.

In the production of an ordinary molding compact, a method such as Ni electroforming is used. However, the original form 11 includes conical or pyramidal shapes each of which has a sharp pointed end. Therefore, in order that the shape can be exactly transferred to the first member 17 of the molding compact 20 and the separation can be performed, four methods are possible as methods allowing for a low-cost manufacture.

The first method is a method in which: a silicone resin including PDMS (polydimethylsiloxane, for example, SYLGARD (registered trademark) 184 manufactured by Dow Corning Corporation) with a curing agent, added thereto is poured into the original form 11; the heat treatment is performed at 100° C. to cure the silicone resin; and the cured silicone resin is separated from the original form 11. The second method is a method in which: a UV (Ultraviolet) curing resin curable by the irradiation with ultraviolet rays is poured into the original form 11; the irradiation with ultraviolet rays is performed in a nitrogen atmosphere; and thereafter the cured resin is separated from the original form 11. The third method is a method in which: a plastic resin such as polystyrene and PMMA (polymethyl methacrylate) dissolved in an organic solvent is poured into the original form 11 on which a release agent has been applied; the organic solvent is volatilized by drying to cure the plastic resin; and the cured plastic resin is separated from the original form 11. The fourth method is a method in which an inverse article is made by Ni electroforming.

Further, other than the four methods, it is possible that the first member 17 of the molding compact 20 is manufactured by the injection molding with use of the original form 11. Moreover, it is possible that the needle-shaped recessed parts are directly formed on a metal plate by an end mill or the like without using the original form 11 and thereby the first member 17 of the molding compact 20 is manufactured.

Taking the first method as an example, the molding compact 20 according to the embodiment of the present invention and the manufacturing method are specifically described.

First, as shown in portion (B) of FIG. 3, for producing the molding compact 20 from the original form 11, a spacer 13 is placed on the edge part of the original form 11, and a thermoset resin 14 is poured. Thereafter, the manufacturing process transits to either of process (I) and process (II) shown in portion (C) to portion (G) of FIG. 3.

In process (I) shown in portion (C) to portion (E) of FIG. 3, a member 15 in which a surface to contact with the thermoset resin 14 is flat is used as a weight, and the heat treatment of the thermoset resin 14 is performed. After the thermoset resin 14 cures by the heat treatment, it is separated from the original form 11. Thereby, the first member 17 on which the needle-shaped recessed parts 16 have been formed is manufactured. The second member 18 composed of a waterproof and moisture-permeable material is laminated on the back surface (the surface on which the needle-shaped recessed parts 16 are not formed) of the first member 17, and further, the third member 19 composed of a rigid body is laminated on the second member 18. Thereby, the molding compact 20 according to the embodiment of the present invention is manufactured.

In process (II) shown in portion (F) to portion (G) of FIG. 3, the second member 18 composed of a waterproof and moisture-permeable material and the third member 19 composed of a rigid body are directly laminated on the thermoset resin 14, and the heat treatment is performed. After the thermoset resin 14 cures by the heat treatment, it is separated from the original form 11. Thereby, the molding compact 20 according to the embodiment of the present invention is manufactured.

Further, in the molding compact 20 according to the embodiment of the present invention, it is preferable that the second member 18 be low in liquid permeability compared to the first member 17 and the third member 19, and the third member 19 be high in rigidity compared to the first member 17 and the second member 18. It is thereby possible to, more suitably, prevent the leakage of the drug-containing solution filled into the needle-shaped recessed parts 16 in the molding compact 20.

Here, it is preferable that the first member 17 and the second member 18 be secured by adhesion or suction.

The molding compact 20 is configured by the adhesion-bonding or pressure-bonding the second member 18 composed of a waterproof and moisture-permeable material that is permeated by air but is not permeated by liquid, to the first member 17. In such the molding compact 20, a gap does not appear on the contact surface between the first member 17 and the second member 18. Therefore, it is possible to prevent the leakage of the drug-containing solution filled into the needle-shaped recessed parts from the contact surface between the first member 17 and the second member 18.

As the material to be used for the first member 17, an elastic material or a metallic material can be used. It is preferable to be an elastic material, and it is further preferable to be a material having a high gas permeability. The oxygen permeability, which is a representative of the gas permeability, preferably, should be greater than $1 \times 10^{-12}$ (mL/s·m²·Pa), and further preferably, should be greater than $1 \times 10^{-10}$ (mL/s·m²·Pa). When the gas permeability is in the above range, it is possible to expel the air present in the needle-shaped recessed parts 16 of the first member 17 from the cast side, and therefore, it is possible to manufacture a transdermal absorption sheet with less defects. As such a material, specifically, there are a silicone resin (for example, SYLGARD (registered trademark) 184, and KE-1310ST (product number) from Shin-Etsu Chemical Co., Ltd.), a UV curing resin and a plastic resin (for example, polystyrene and PMMA (polymethyl methacrylate)) that are melted or are dissolved in a solvent, and the like. Among them, a silicone rubber type material has a durability against the transfer by repetitive compression, and has a good separation property for the material, allowing for a suitable use. Further, as the metallic material, there are Ni, Cu, Cr, Mo, W, Ir, Tr, Fe, Co, MgO, Ti, Zr, Hf, V, Nb, Ta, α-aluminum oxide, zirconium oxide, stainless steel (for example, STAVAX (registered trademark) from Bohler-Uddeholm KK) and the like, and alloys thereof.

Furthermore, preferably, the air permeability (air resistance) of the second member 18 and the third member 19, which is measured according to the Gurley tester method described in JIS P8117 (2009 edition), should be 3 seconds/100 cm³ or more and 100 seconds/100 cm³ or less.

When the air permeability of the second member 18 and the third member 19 is 3 seconds/100 cm³ or more, the solution is easily filled into the needle-shaped recessed parts 16 of the first member 17, resulting in a good productivity. Further, when the air permeability of the second member 18 and the third member 19 is 100 seconds/100 cm³ or less, the second member is hard to tear due to the suction at the time of the manufacture of the transdermal absorption sheet and the solution is unlikely to leak. Further, when the air permeability is 100 seconds/100 cm³ or less, the adhesiveness with the first member is good, which enables stable manufacture. Here, the air permeability of the second member 18 and the third member 19, preferably, should be 0.1 seconds/100 cm³ or more and 80 seconds/100 cm³ or less, and further preferably, should be 0.5 seconds/100 cm³ or more and 50 seconds/100 cm³ or less.

Further, it is preferable that the waterproof and moisture-permeable material of the second member 18 be a porous material having a pore size of 0.1 μm or more and 2.0 μm or less.

When the pore size of the second member 18 is 0.1 μm or more, the permeability of air is good, the filling of the solution is easy, and the productivity is good. Further, when the pore size of the second member 18 is 2.0 μm or less, the deformation of the first member 17 due to the suction can be prevented at the time of the manufacture of the transdermal absorption sheet to thereby prevent the leakage of the solution, even if the first member 17 is composed of a soft material such as silicone rubber.

Here, as the waterproof and moisture-permeable material of the second member 18, for example, GORE-TEX (registered trademark), TEMISH (registered trademark) or the like can be suitably used.

Figure 4:
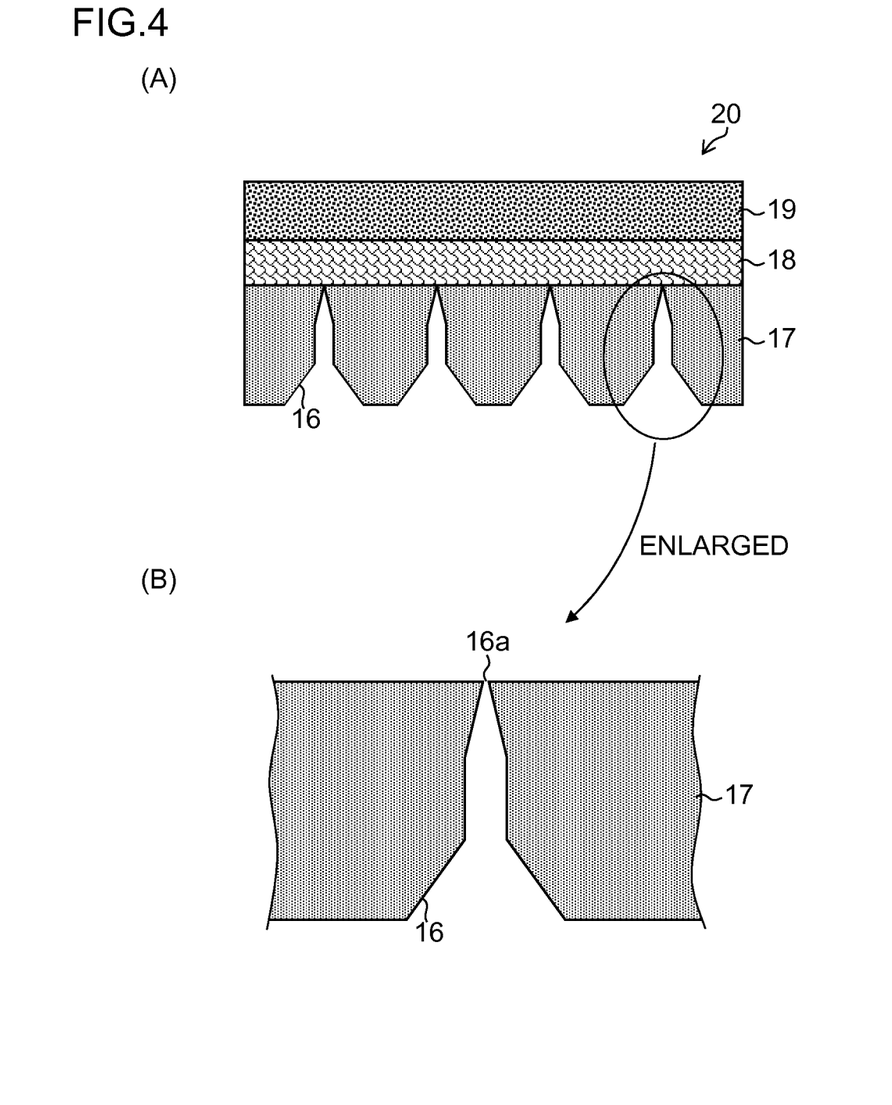
FIG. 4 is a cross-section view of the molding compact according to the present invention and an enlarged view of a needle-shaped recessed part.

Portion (A) of FIG. 4 is a diagram showing the molding compact 20 according to the embodiment of the present invention. Portion (B) of FIG. 4 is an enlarged view of the portion surrounded by the circle (the first member 17 on which the needle-shaped recessed part 16 is formed), in portion (A).

It is preferable that a through hole 16a having a size of 1 μm or more and 50 μm or less be formed at the pointed end of the needle-shaped recessed part 16 of the first member 17. Since the through hole 16a having a size of 1 μm or more and 50 μm or less is formed at the pointed end of the needle-shaped recessed part of the first member 17, even when air stays in the needle-shaped recessed part 16 of the first member, the air easily comes out. When the size of the through hole is 1 μm or more, the drug-containing solution is easily infused into the needle-shaped recessed part so that the productivity is improved. Further, when the size of the through hole is 50 μm or less, the needling into the skin can be performed with no pain, because the pointed end of the needle of the manufactured transdermal absorption sheet has a size of 50 μm or less. Here, the size of the through hole, more preferably, should be 10 μm or more and 50 μm or less, and further preferably, should be 15 μm or more and 45 μm or less. The molding compact 20 produced in this way can be easily produced any number of times, with the original form 11.

Figure 5:
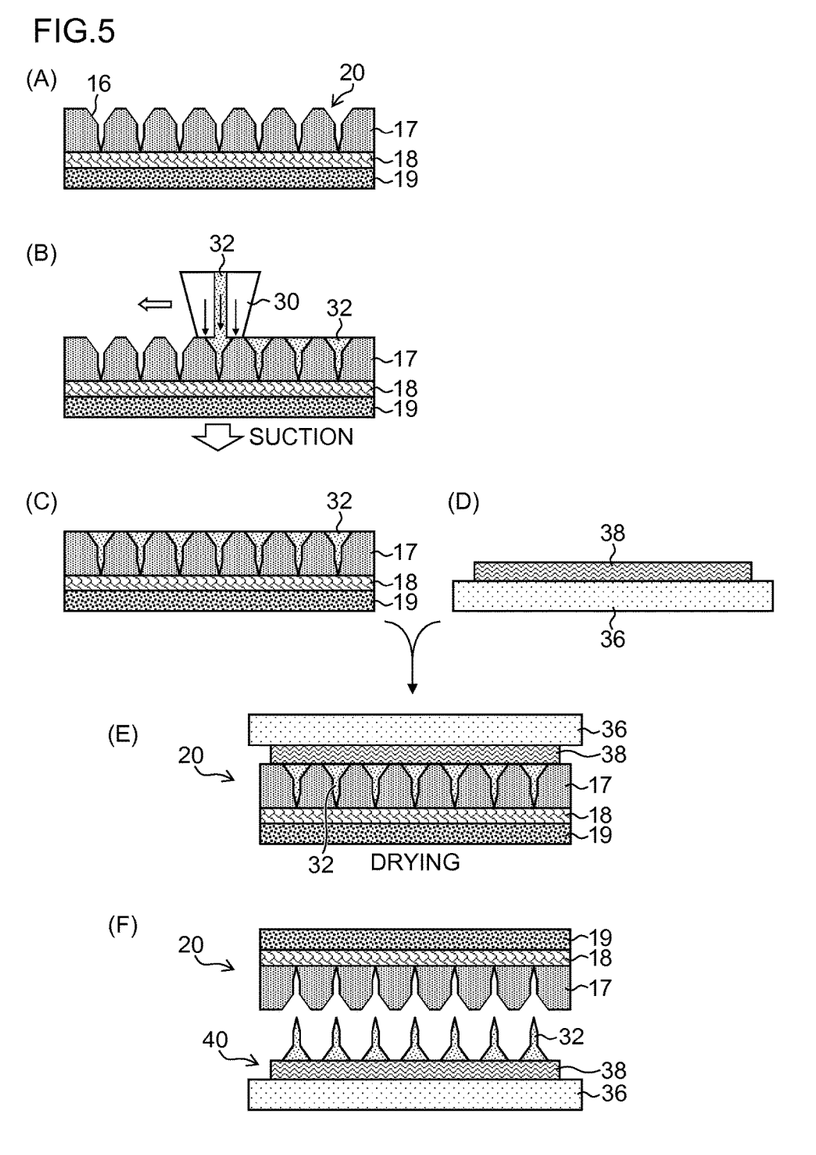
FIG. 5 is a process drawing showing an example of a manufacturing method for a transdermal absorption sheet according to the present invention.

Next, an example of the method for manufacturing the transdermal absorption sheet with the molding compact 20 according to the present invention is described with FIG. 5.

First, the molding compact 20 manufactured in the above way is placed (portion (A) of FIG. 5).

Next, a polymer resin solution is applied on the molding compact 20. Specifically, as shown in portion (B) of FIG. 5, a polymer solution 32 in which a polymer resin is dissolved is filled into the needle-shaped recessed parts 16 (corresponding to the micro-needles) of the produced molding compact 20. The method for filling the solution can be performed without being particularly limited, but it is preferable that an application method with a nozzle 30 be used as shown in portion (B) of FIG. 5. Alternatively, a bar coating method, a spin coating method or an application with a spray or the like can be used. In the case of the application with the nozzle 30, the nozzle 30 moves while contacting with the first member 17 of the molding compact 20, and supplies the solution 32. It is thereby possible to suitably fill the solution 32 into the needle-shaped recessed parts 16.

In the filling of the solution, it is preferable that vacuum suction be performed from the back surface of the third member 19 of the molding compact 20. Since the suction is performed from the side of the third member 19 composed of a rigid body, even when air stays in the needle-shaped recessed part, it is possible to stably remove the air.

It is preferable that the first member 17 and the second member 18 of the molding compact 20 be secured by adhesion or suction. The molding compact is configured by the adhesion-bonding or pressure-bonding the second member composed of a waterproof and moisture-permeable material which allows permeation of air but not of liquid, to the first member. In such the molding compact, a gap does not appear on the contact surface between the first member and the second member. Therefore, it is possible to prevent the leakage of the drug-containing solution filled into the needle-shaped recessed parts from the contact surface between the first member and the second member.

It is preferable that a resin having biocompatibility be used as the material of the resin polymer to be used for the polymer solution. As such a resin, it is preferable to use a saccharide such as glucose, maltose, pullulan, hydroxyethyl starch, sodium hyaluronate and sodium chondroitin sulfate, a protein such as gelatin, or a biodegradable polymer such as polylactic acid and lactic acid-glycolic acid copolymer. Although the concentration varies depending on the material, it is preferable to be such a concentration that 10 to 50 wt % resin polymer is contained in the solution. Further, the solvent to be used for the dissolution may be other than warm water if it has volatility, and methyl ethyl ketone (MEK), alcohol or the like can be used.

Then, depending on the use, a drug to be supplied into the body is dissolved together in the polymer resin solution. The drug to be contained in the solution is not limited if it has a function as a drug, and it is preferable to select from peptide, protein, nucleic acid, polysaccharide, vaccine, medical compounds belonging to aqueous low molecular weight compounds, or cosmetic ingredients.

The viscosity of the polymer resin solution, preferably, should be 100 Pa·s or less, and more preferably, should be 10 Pa·s or less. When the viscosity of the polymer resin solution is in the above range, the solution is easily infused into the recessed parts.

As for the preparation method for the polymer solution, in the case of using an aqueous high-polymer (gelatin or the like), it can be manufactured by dissolving aqueous powder in water and adding a drug after the dissolution.

Next, a support 36 shown in portion (D) of FIG. 5 on which a polymer resin solution 38 has been applied is overlaid on the molding compact 20 filled with the polymer solution 32 shown in portion (C) of FIG. 5 (portion (E) of FIG. 5). As the polymer solution 38 shown in portion (D) of FIG. 5, it is preferable to use a solution left after removing the drug from the polymer solution 32 that is filled into the needle-shaped recessed parts 16 of the molding compact 20.

The coating apparatus to apply the solution 38 onto the support 36 is not particularly limited, and it is preferable to be a measurement type coating apparatus that facilitates the application of a constant amount of solution, as exemplified by a slot coater, a rod coater, a knife coater and a gravure coater.

Subsequently, the drying of the polymer solutions 32, 38 is performed in a state shown in portion (E) of FIG. 5. Specifically, for example, it is possible to perform the drying by blowing warm air to the polymer solutions.

As the drying method, warm air is blown at 0.1 to 20 m/s. For example, it is preferable that the warm air be at 35° C. and have a relative humidity of 40% or less.

Further, in the flowing of the high-temperature warm air for the drying, when the temperature of the warm air is too high, depending on the drug, the efficacy of the drug may change due to the degradation by the heating. Therefore, attention is required to the temperature of the warm air to be blown. In this way, the applied polymer solutions are dried, and thereby, the polymer solutions solidify. By the solidification of the resin polymers, the polymer solutions shrink relative to the state at the time of the application. This facilitates the separation from the molding compact 20. Further, when the water content of the resin polymer becomes too low in this step, it is hard to perform the separation. Therefore, it is preferable to save a water content allowing the elasticity to be maintained. Specifically, although depending on the material composing the resin polymer, it is preferable that the drying be stopped when the water content has become 10 to 20 wt %, or the air be blown at 25° C. and at a relative humidity of about 40%.

Next, the separation is performed. Specifically, as shown in portion (F) of FIG. 5, the support 36 is stripped off from an edge part, and thereby, the separation is performed. Thus, a transdermal absorption sheet 40 can be manufactured.

The step of separating the aggregate of the cured resin polymer from the molding compact 20 is an important step. Typically, when the micro-needle structure having a high aspect ratio is separated from the molding compact 20 as shown in the embodiment, a strong stress is applied because the contact area is large. As a result, there is a fear that the micro-needle is broken, is not separated from the molding compact 20, and remains in the needle-shaped recessed part 16 of the molding compact 20 so that the produced transdermal absorption sheet has a fatal defect. In light of this point, in the embodiment, it is preferable that the material to compose the first member 17 of the molding compact 20 be constituted by a material which is extremely releasable. Further, when the material to compose the first member 17 of the molding compact 20 is a high-elastic and soft material, it is possible to lessen the stress to be applied to the micro-needles at the time of the separation.

By manufacturing in this way, the drug-containing solution filled into the needle-shaped recessed parts does not leak in the manufacturing process, and therefore, it is possible to provide a transdermal absorption sheet with no defect.

Here, for vaporizing the water remaining in the micro-needles on the front surface of the resin polymer, in some cases, the dry air is blown again after the separation. Specifically, it is preferable to make the water content in the resin polymer be 10 wt % or less, preferably 5 wt % or less, just before the packing, and thereafter the product is packed.

Further, the molding compact can be utilized multiple times, and therefore, by repeating the steps in FIG. 5 with use of the cast after the separation, it is possible to produce multiple transdermal absorption sheets in a short time.

It should be noted that the present invention is not limited to the above embodiment, and the embodiment can be appropriately changed within the range of the technical idea of the present invention.

What is claimed is:

1. A molding compact for forming a transdermal absorption sheet on which a needle-shaped protruding parts are arranged, the molding compact configured by laminating:
   a first member having needle-shaped recessed parts formed on a front surface thereof, the needle-shaped recessed parts being an inverse of the needle-shaped protruding parts;
   a second member provided on a back surface of the first member, the second member being composed of a waterproof and moisture-permeable material; and
   a third member provided on a back surface of the second member, the third member being composed of a rigid body, wherein an air permeability of the second member and the third member is 3 seconds/100 cm$^3$ or more and 100 seconds/100 cm$^3$ or less, and wherein the air permeability of the second member and the third member is measured according to a Gurley tester method described in JIS P8117 (2009 edition).

2. The molding compact according to claim 1,
wherein the waterproof and moisture-permeable material of the second member is a porous material having a pore size of 2.0 μm or less.

3. The molding compact according to claim 2,
wherein the waterproof and moisture-permeable material of the second member is a porous material having a pore size of 0.1 μm or more.

4. The molding compact according to claim 1,
wherein the second member is low in liquid permeability compared to the first member and the third member, and the third member is high in rigidity compared to the first member and the second member.

5. The molding compact according to claim 1,
wherein through holes each having a size of 1 μm or more and 50 μm or less are formed at pointed ends of the needle-shaped recessed parts of the first member.

6. The molding compact according to claim 1,
wherein the first member and the second member are secured by adhesion or suction.

7. The molding compact according to claim 1,
wherein through holes each having a size of 15 μm or more are formed at pointed ends of the needle-shaped recessed parts of the first member.

8. A manufacturing method for a transdermal absorption sheet comprising:
a step of filling a solution obtained by mixing a drug and a polysaccharide, into the needle-shaped recessed parts of the molding compact according to claim 1;
a step of making a solidified matter by drying and solidifying the solution filled into the molding compact; and
a step of separating the solidified matter from the molding compact.

9. The manufacturing method for a transdermal absorption sheet according to claim 8,
wherein vacuum suction is performed from a back surface of the third member of the molding compact, in the step of filling the solution.

* * * * *